(12) United States Patent
Nautiyal et al.

(10) Patent No.: US 6,638,730 B2
(45) Date of Patent: Oct. 28, 2003

(54) COMPOSITION FOR QUALITATIVE SCREENING OF PHOSPHATE SOLUBILIZING MICROORGANISMS AND A QUALITATIVE METHOD FOR SCREENING MICROORGANISMS

(75) Inventors: Chandra Shekhar Nautiyal, Uttar Pradesh (IN); Sangeeta Mehta, Uttar Pradesh (IN); Palpu Pushpangadan, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 161 days.

(21) Appl. No.: 09/798,955

(22) Filed: Mar. 6, 2001

(65) Prior Publication Data

US 2002/0172993 A1 Nov. 21, 2002

(51) Int. Cl.$^7$ .................................................. C12Q 1/04
(52) U.S. Cl. ........................... 435/34; 435/4; 435/7.31; 435/7.32; 435/39; 435/253.6; 435/254.2
(58) Field of Search ...................... 435/4, 7.31, 7.32, 435/34, 39, 253.6, 254.2

(56) References Cited

PUBLICATIONS

H.W. Johnston, et al., "I.–The Action of Various Organic Compounds of Dicalcium and Tricalcium Phosphates", The Solubilization of Phosphate, pp, 436–446 (1952).
R.E., Rose, et al., "Techniques for Determining the Effect of Microorganisms on Insoluble Inorganic Phosphates", N.Z. Journal of Science and Technology, pp. 773–780 (1957).
K.S. Yadav, et al., "Phosphate Solubilization and Mobilization through Soil Microorganisms", Scientific Publishers, pp. 292–308 (1997).
C.L. Wenzel, et al., "Phosphate–solubilizing bacteria associated with proteoid roots of seedlings of waratah [*Telopea speciosissima* (Sm.) R.Br.]," New Phytol., vol. 128, pp. 487–496 (1994).
David L. Jones, et al., "Role of root derived organic acids in the mobilization of nutrients from the rhizosphere", Plant and Soil, vol. 166, pp. 247–257 (1994).
M.H. Abd–Alla, "Phosphatases and the utilization of organic phosphorus by *Rhizobium leguminosarum* biovar viceae", Letters in Applied Microbiology, vol. 18, pp. 294–296 (1994).
Rani Gupta, et al., "A Modified Plate Assay for Screening Phosphate Solubilizing Microorganisms", J. Gen. Appl. Microbiol., vol. 40, pp. 255–260, (1994).
C. Leyval, et al., "Interactions between *Laccaria laccata, Agrobacterium radiobacter* and beech roots; Influence on P, K, Mg, and Fe mobilization from minerals and plant growth", Plant and Soil, vol. 117, pp. 103–110 (1989).
C. Shekhar Nautiyal, et al., "Stress induced phosphate solubilization in bacteria isolated from alkaline soils", FEMS Microbiology Letters, vol. 182, pp. 291–296 (2000).
Jayandra Kumar Johri, et al., "Occurence of Salt, pH, and Temperature–tolerant, Phosphate, solubilizing Bacteria in Alkaine Soils", Current Microbiology, vol. 39, pp. 89–93 (1999).
Sunita Gaind, et al., "Effect on pH on Phophate Solubilization by Microbes", Current Science, vol. 58, No. 21, pp. 1208–1211 (1989).
R. P. Sethi, et al., "Solubilization of Tricalcium Phosphate and Calcium Phytate by Soil Fungi", J. Gen. Appl. Microbiol., vol. 14, pp. 329–331 (1968).
A.K. Halder, et al., "Solubilization of inorganic phosphates by *Bradyhizobium*", Indian Journal of Experimental Biology, vol. 29, pp. 28–31, (1991).
P. D. Bajpai, et al., "Phosphate Solubising Bacteria, Part II. Extracellular Production of organic Acids by Selected Bacteria Solubilising Insoluble Phosphate", Division of Microbiology Indian Agricultural Research Institute, pp. 44–45 (1969).
C. Shekhar Nautiyal, "An efficient microbiology growth medium for screening phosphate solubilizing microorganisms", FEMS Microbiology Letters, vol. 170, pp. 265–270 (1999).
W. V. B. Sundara, et al., "Phosphate Dissolving Micro–Organisms in the Soil and Rhizosphere", Indian J. Agric. Sci., vol. 33, No. 4, pp. 272–278 (1963).
R. I. Pikovskaya, "Mobilization of Phosphates in Soil in Connection With Metabolic Processes of Some Microbial Species", Microbiology, vol. 17, pp. 362–370 (1948). English translation provided.

*Primary Examiner*—Dwayne C. Jones
*Assistant Examiner*—C. Delacroix-Muirheid
(74) *Attorney, Agent, or Firm*—Piper Rudnick LLP; Steven B. Kelber

(57) ABSTRACT

The present invention relates to a composition useful for qualitative screening of phosphate solubilizing microorganism, and also relates to a synergistic composition for qualitative screening of phosphate solubilizing microorganisms, based upon visual observation.

15 Claims, 4 Drawing Sheets

COMPOSITION FOR QUALITATIVE SCREENING OF PHOSPHATE SOLUBILIZING MICROORGANISMS AND A QUALITATIVE METHOD FOR SCREENING MICROORGANISMS

FIELD OF THE INVENTION

The present invention relates to a synergistic composition useful for qualitative screening of phosphate solubilizing microorganisms. More particularly, the present invention provides synergistic composition for qualitative screening of phosphate solubilizing microorganisms, based upon visual observation.

BACKGROUND AND PRIOR ART

A large portion of inorganic phosphates applied to soil as fertiliser is rapidly immobilised after application and becomes unavailable to plants (Yadav K S, Dadarwal K R (1997) Phosphate solubilisation and mobilisation through soil microorganisms. In: Dadarwal K R (ed): Biotechnological approaches in soil microorganisms for sustainable crop production. Jodhpur, India: Scientific Publishers, pp. 293–308. Thus, the release of insoluble and fixed forms of phosphorus is an important aspect of increasing soil phosphorus availability. Seed or soil inoculation with phosphate solubilizing bacteria is known to improve solubilisation of fixed soil phosphorus and applied phosphates resulting in higher crop yields. [Abd-Alla M H (1994) Phosphatases and the utilisation of organic phosphorus by *Rhizobium leguminosarum* biovar viceae. Lett Appl Microbiol 18:294–296; Jones D L, Darrah P R (1994) Role of root derived organic acids in the mobilisation of nutrients from the rhizosphere. Plant Soil 166:247–257; Leyval C, Barthelin J (1989) interactions between *Laccaria laccata, Agrobacterium radiobacter* and beech roots: Influence on P, K, Mg and Fe mobilisation from mineral and plant growth. Plant Soil 17:103–110; Yadav K S, Dadarwal K R (1997) Phosphate solubilisation and mobilisation through soil microorganisms. In: Dadarwal K R (ed). Biotechnological approaches in soil microorganisms for sustainable crop production. Jodhpur, India: *Scientific Publishers*, pp. 293–308j. Several authors attribute the solubilisation of inorganic insoluble phosphate by microorganisms to the production of organic acids and chelating oxo acids from sugars [Leyval C, Barthelin J (1989) Interactions between *Laccaria laccata, Agrobacterium radiobacter* and beech roots: Influence on P, K, Mg and Fe mobilisation from mineral and plant growth. Plant Soil 17:103–110; Yadav K S, Dadarwal K R (1997) Phosphate solubilisation and mobilisation through soil microorganisms. In: Dadarwal K R (ed): Biotechnological approaches in soil microorganisms for sustainable crop production. Jodhpur, India: Scientific Publishers, pp. 293–308]. Therefore, most of the quantitative tests to assay the relative efficiency of the phosphate solubilizing bacteria are based on the lowering of pH, due to production of organic acids into the surrounding medium [Bajpai P D, Sundara Rao W V B (1971) Phosphate solubilizing bacteria II. Extracellular production of organic acids by selected bacteria solubilizing insoluble phosphates. Soil Sci Plant Nutr 17:44–45; Gaind S, Gaur A C (1989) Effect of pH on phosphate solubilisation by microbes. Curr Sci 58:1208–1211; Johnston H W (1952) The solubilisation of phosphate: the action of various organic compounds on dicalcium and tricalcium phosphate. NZJ Sci Technol 33:436–444; Rose R E (1957) Techniques of determining the effect of microorganisms on insoluble inorganic phosphates. N.Z.J Sci Technol 38:773–780; Sethi R P, Subba Rao N S (1968) Solubilisation of tricalcium phosphate and calcium phytase by soil fungi. J Gen Appl Microbiol 14:329–331]. The initial isolation of phosphate solubilisers is usually made by using a medium suspended with insoluble-phosphates such as tri-calcium phosphates [Tilak K V B R (1993) Bacterial Fertilisers. New Delhi, India: Indian Council of Agricultural Research]. The production of clearing zones around the colonies of the organism is an indication of the presence of phosphate solubilizing organisms. Such cultures are isolated and extent of phosphate solubilisation determined quantitatively, using biochemical methods (Tilak K V B R (1993) Bacterial Fertilisers. New Delhi, India: Indian Council of Agricultural Research; Subba Rao N S (1993) Biofertilizers in agriculture and forestry. Oxford & IBH Publishing Company Pvt. Ltd., New Delhi: Oxford & IBH Publishing Company Pvt Ltd.].

Phosphate solibilising microorganisms are routinely screened by a plate assay method using Pikovskaya (PVK containing (gm/Lt): glucose, 10; $Ca_3(PO_4)_2$, 5; $(NH_4)_2SO_4$, 0.5; NaCl, 0.2; $MgSO_4.7H_2O$, 0.1; KCl, 0.2; yeast extract, 0.5; $MnSO_4.H_2O$, 0.002 and $FeSO_4.7H_2O$, 0.002) agar [Pikovskaya R I (1948) Mobilisation of phosphorus in soil in connection with the vital activity of some microbial species. Mikrobiologiya 17:362–370]. Other phosphate solibilising media known in the prior art besides PVK are as follows containing (gm/Lt): 1. Glucose, 10; $CaHPO_4$ 5, yeast extract, 0.5; KCl, 0.2; $MgSO_4.7H_2O$, 0.1; $MnSO_4$, trace; and $FeSO_4.7H_2O$, trace [Sundara Rao, W V M, Sinha M K (1963) Phosphate dissolving organisms in soil and rhizosphere. Ind. J. Agri. Sci. 33, 272–278].

2. Glucose, 10; $Ca_3(PO_4)_2$, 5; $(NH_4)_2SO_4$, 1; $MgSO_4.7H_2O$, 0.5; KCl, 0.2; yeast extract, 0.2; $MnSO_4.H_2O$, trace and $FeCl_3$, trace [Halder A K, Mishra A K, Chakarbartty P K (1991) Solubilisation of inorganic phosphates by Bradyrhizobium Ind. J. Exp. Biol. 29, 28–31].

3. Sucrose, 5; $CaHPO_4$, 5; $MgSO_4.7H_2O$ 0.5; $KNO_3$, 1; KCl, 0.5; and $FeSO_4.7H_2O$, 0.011 [Wenzel, C. L., Ashford, A. E. and Summerell, B. A. (1994) Phosphate solubilizing bacteria associated with protoid roots of seedlings of waratoh (*Telopea speciosissama.*) New Phytol. 128, 487–496].

4. Mannitol, 10: Hydroxyapetite, 2; $NH_4Cl_2$, 1; $MgSO_4.7H_2O$, 0.5; KCl, 0.2; biotin, 0.001; calcium pantothenate. 0.001; $MnSO_4.H_2O$, 0.002 and $FeCl_3$, 0.002 [Abd-Alla M H (1994) Phosphatases and the utilisation of organic phosphorus by *Rhizobium leguminosarum* biovar viceae. Lett Appl Microbiol 18:294–296].

The test of the relative efficiency of isolated strains is carried out by selecting the microorganisms which are capable of producing a halo/clear zone on plate due to the production of organic acids into the surrounding medium [Pikovskaya R I (1948) Mobilisation of phosphorus in soil in connection with the vital activity of some microbial species. Mikrobiologiya 17:362–370].

However, as the reliability of this halo-based technique is questioned as many isolates which did not produce any visible halo/zone on agar plates could solubilise various types of insoluble inorganic phosphates in liquid medium a modified PVK medium using bromophenol blue (BPB), to improve the clarity and visibility of the yellow-coloured halo has not necessarily improved the plate assay [Gupta R, Singal R, Shankar A, Kuhad R C Saxena R K (1994) A modified plate assay for screening phosphate solubilizing microorganisms. J Gen Appl Microbiol 40:255–260]. Thus, the existing plate assay fails where the halo is inconspicuous or absent. Contrary to indirect measurement of phosphate solubilisation by plate assay, the direct measurement of phosphate solubilisation in broth assay always resulted into reliable results [Nautiyal C S (1999) An efficient microbiological growth medium for screening phosphate solubilizing microorganisms. FEMS Microbiol Lett 170:265–270]. It was suggested that microbes from soil may be screened in National Botanical Research Institute's phosphate growth medium (NBRIP) broth assay for the identification of most efficient phosphate solubilisers [Johri J K. Surange S Nautiyal C S (1999) Occurrence of salt, pH and temperature-tolerant, phosphate-solubilizing bacteria in alkaline soils. Curr Microbiol 39:89–93; Nautiyal C S, Bhadauria S, Kumar P, Lal H, Mondal R, Verma D (2000) Stress induced phosphate solubilisation in bacteria isolated from alkaline soils. FEMS Microbiol Lett 182:291–296]. NBRIP contained (per liter): glucose, 10 g; $Ca_3(PO_4)_2$, 5 g; $MgCl_2.6H_2O$, 5 g; $MgSO_4.7H_2O$, 0.25 g; KCl, 0.2 g, and $(NH_4)_2SO_4$, 0.1 g [Nautiyal C S (1999) An efficient microbiological growth medium for screening phosphate solubilizing microorganisms. FEMS Microbiol Lett 170:265–270].

However, screening large number of isolates for phosphate solubilisation by quantitative methods requires investment of time, labour and chemicals. Thus BPB a blue coloured dye which decolorises due to drop in pH of the medium was used, as an indicator to quickly evaluate the level of phosphate solubilisation based upon visual observations.

Therefore, it is desirable to formulate a defined media for screening phosphate solubilizing microorganisms, based upon visual observations, to quickly evaluate the level of phosphate solubilisation.

OBJECT OF THE INVENTION

The main object of the present invention is to provide a synergistic composition which is based upon visual observations, and not on quantitative analysis involving investment of time, labour and chemicals, to quickly evaluate the level of phosphate solubilisation

DETAILED DESCRIPTION OF THE INVENTION

Accordingly the present invention provides a synergistic composition containing BPB designated, "NBRI-BPB" which comprises:

| | |
|---|---|
| glucose | 5 to 30 gm/Lt; |
| $Ca_3(PO_4)_2$, | 1 to 20 gm/Lt; |
| $MgCl_2.6H_2O$ | 0.5 to 20 gm/Lt; |
| $MgSO_4.7H_2O$ | 0.05 to 5 gm/Lt; |
| KCl, | 0.025 to 5 gm/Lt; |
| $(NH_4)_2SO_4$ | 0.01 to 2 gm/Lt; and |
| BPB | 0.01 to 0.1 gm/Lt. |

In an embodiment of the present invention, the ingredients used in the synergistic composition of the present invention may be of commercial grade. However, the use of purer ingredients such as that of laboratory grade will result in better reproducible results.

The synergistic composition of the present invention is not a mere admixture of the ingredients used resulting in aggregation of their properties but a synergistic mixture having enhanced properties resulting in identifying phosphate solubilizing microorganisms.

In one embodiment, the invention provides a qualitative method for easy and fast screening of phosphate solubilizing comprising a synergistic growth medium composition containing essential bromophenol blue (BPB) in the range of 0.01 to 0.1 gm/Lt.

In another embodiment of the present invention a kit for the screening of phosphate solubilizing microorganisms comprising BPB in a growth medium, comprising:

| | |
|---|---|
| Glucose | 10 gm/Lt.; |
| $Ca_3(PO_4)_2$ | 5 gm/Lt.; |
| $MgCl_2.6H_2O$ | 5 gm/Lt.; |
| $MgSO_4.7H_2O$ | 0.25 gm/Lt.; |
| KCl | 0.2 gm/Lt.; |
| $(NH_4)_2SO_4$ | 0.1 gm/Lt.; and |
| BPG | 0.025 gm/Lt. |

The synergistic composition of the present invention may be prepared by any one of the known methods.

BRIEF DESCRIPTION OF THE ACCOMPANYING DRAWINGS

FIG. 1 shows Qualitative (■) and quantitative (□) analysis of bacterial strains ASLU 13 (A,C,E,G) and $N_3$ (B,D,F,H) grown in NBRIP medium containing 0.01 (A,B);0.025 (C,D); 0.05 (E,F) and 0.01 (G,H) gm/l of bromophenol blue at 30° C., pH 7 for 7 days.

Figure 1:
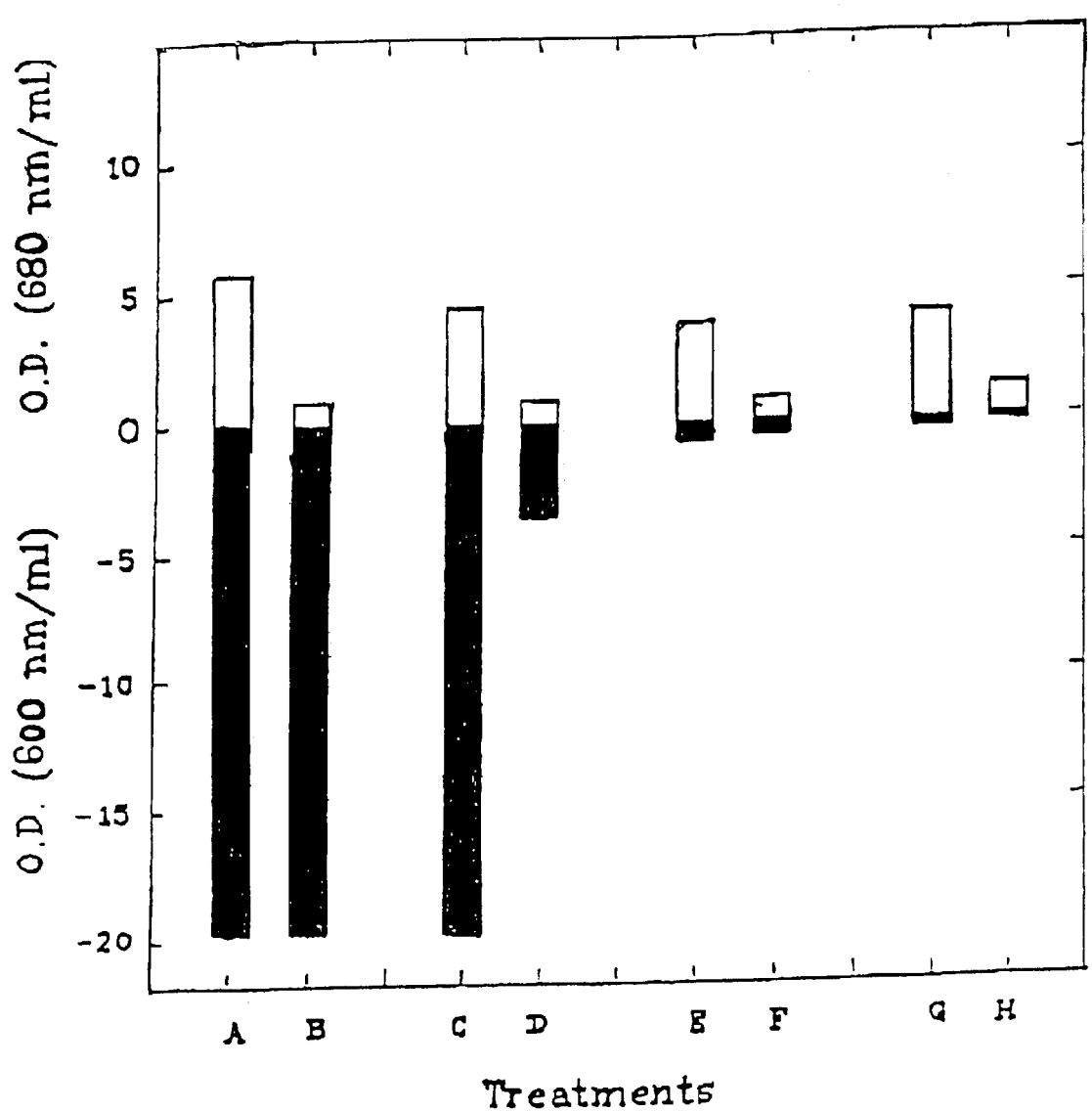

In our attempt to reduce the time required to perform quantitative assay we modified NBRIP medium by using BPB as an indicator dye for visual observations, to quickly evaluate the level of phosphate solubilisation. The results are shown in FIG. 1 of the drawing accompanying this specification. Qualitative (■) and quantitative (□) analysis of bacterial strains ASLU13 (A, C, E, G) and N3 (B, D, F, G) grown in NBRIP medium, containing 0.01 (A. B); 0.025 (C, D): 0.05 (E. F) and 0.1 (G, H) gm/Lt of bromophhenol blue, at 30° C., pH 7 for 3 days.

It was of interest to compare the influence of BPB on qualitative and quantitative analysis, using bacterial strains ASLU13 (an efficient phosphate solubilizer) and N3 (a moderately efficient phosphate solubilizer) grown in NBRIP liquid medium containing 0.01, 0.025, 0.05 and 0.1 gm/Lt BPB, for 3 days (FIG. 1). Highest limit of decolorisation (−1.999 O. D. at 600 nm) in the presence of 0.01 (FIG. 1A) and 0.025 (FIG. 1C) gm/Lt BPB by ASLU13 was achieved by day 3. For N3 the highest limit of decolorisation of BPB was achieved for 0.01 gm/Lt BPB (FIG. 1B), while it declorised 0.025 gm/Lt BPB to −0.25 O. D. by day 3 (FIG. 1D). Our data show that it is possible to distinguish among ASLU13 and N3 based on quantitative analysis, using 0.025 gm/Lt BPB (FIG. 1). It was observed that, NBRIP liquid medium containing 0.01, 0.025, 0.05 and 0.1 gm/Lt BPB, had no appreciable effect on quantitative analysis of phosphate solubilisation, by ASLU13 and N3 (FIG. 1). However, based on qualitative analysis increasing the concentration of BPB to more than 0.025 gm/Lt, unlike quantitative analysis, it was not possible to distinguish among ASLU13 and N3 (FIG. 1). Therefore, concentration of 0.025 gm/Lt BPB was used to formulate the new medium. This National Botanical Research Institute's phosphate growth medium containing 0.025 gm/Lt BPB, was designated as NBRI-BPB.

Based on the observations obtained as above the novel synergistic composition of the present invention NBRI-BPB was defined, which comprises:

| | |
|---|---|
| glucose | 10 gm/Lt; |
| $Ca_3(PO_4)_2$, | 5 gm/Lt; |
| $MgCl_2.6H_2O$ | 5 gm/Lt; |
| $MgSO_4.7H_2O$ | 0.25 gm/Lt; |
| KCl, | 0.2 gm/Lt; |
| $(NH_4)_2SO_4$ | 0.1 gm/Lt; and |
| BPB | 0.025 gm/Lt. |

The invention is described with reference to the examples which are provided by way of illustration only and these should not be be construed to limit the scope of the present invention.

EXAMPLE 1

Figure 2:
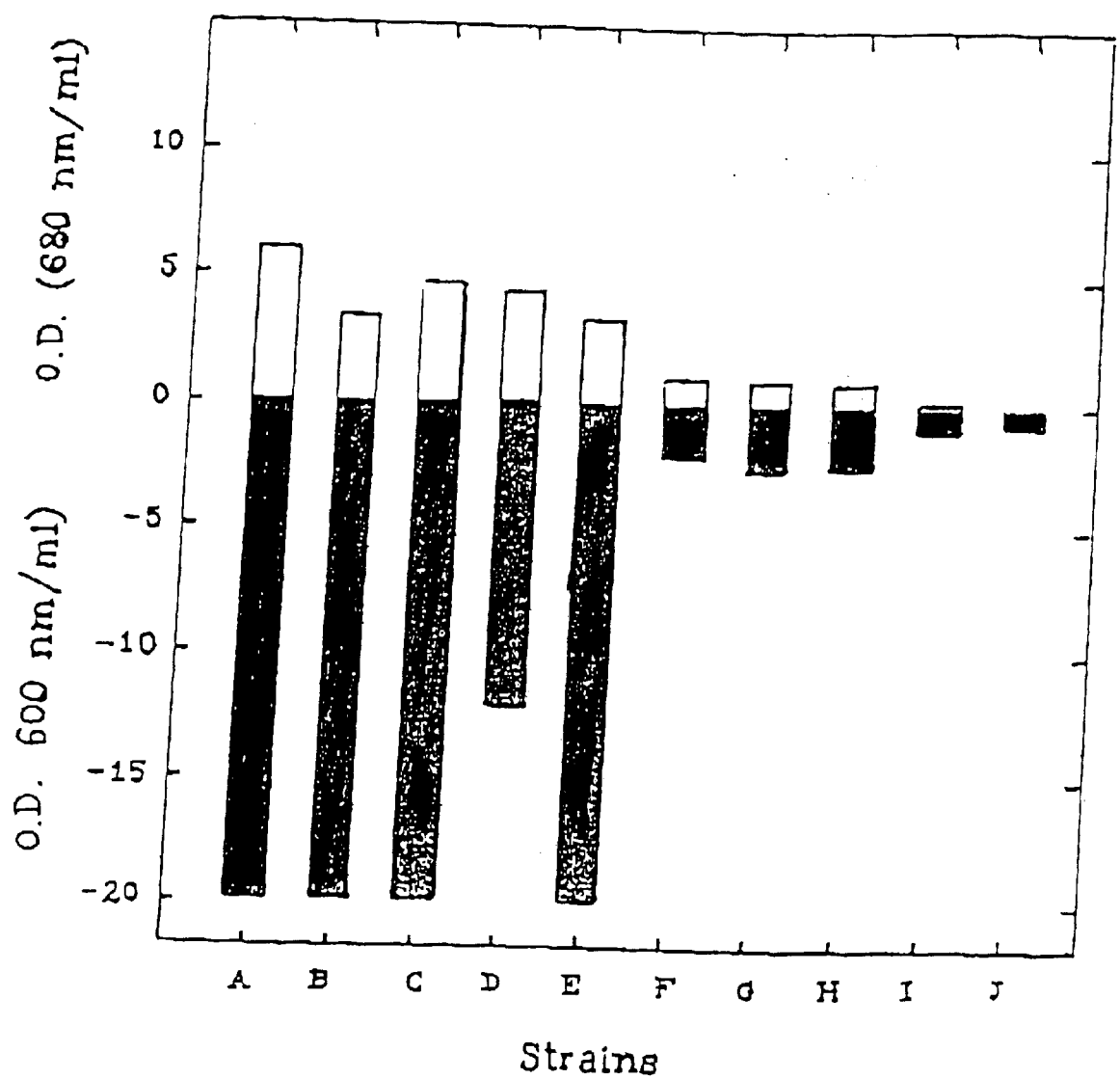
FIG. 2 shows Qualitative (■) and quantitative (□) analysis of bacterial strains ASLU 13 (A), 12.33 (B), AS7.8 (C), 2661 (D), 2346(E), 4003 (F), N (G), P (H), SN15 (I) and SN 16(J) grown in NBRI-BPB medium at 30° C., pH 7 for 3 days.

Potential of NBRI-BPB to evaluate large number of phosphate solubilisers was tested by initial screening of 2015 bacterial strains. Based upon the quantitative assay ten bacterial strains, ASLU13, 12.33, AS7.8, 2661, 3246, 4003, N, P, SN15, and SN16 were selected for further work. The results are shown in FIG. 2 of the drawing accompanying this specification. Qualitative (■) and quantitative (□) analysis of ten bacterial strains, ASLU13 (A), 12.33 (B), AS7.8 (C), 2661 (D), 3246 (E), 4003 (F), N (G), P (H), SN15 (I), and SN16 (J) grown in NBRI-BPB medium, at 30° C., pH 7 for 3 days.

Qualitative and quantitative analysis was carried out using ten bacterial strains, ASLU13 (FIG. 2A), 12.33 (FIG. 2B), AS7.8 (FIG. 2C), 2661 (FIG. 2D), 3246 (FIG. 2E), 4003 (FIG. 2F), N (FIG. 2G), P (FIG. 2H), SN15 (FIG. 2I), and SN16 (FIG. 2J) grown on NBRI-BPB, for 3 days. The strains selected could be placed into two distinct groups based upon the level of phosphate solubilisation. First group of five strains ASLU13 (FIG. 2A), 12.33 (FIG. 2B), AS7.8 (FIG. 2C), 2661 (FIG. 2D), and 3246 (FIG. 2E) solubilised phosphate was at least 3-fold more efficient than that of second group of five strains 4003 (FIG. 2F), N (FIG. 2G), P (FIG. 2H), SN15 (FIG. 2I), and SN16 (FIG. 2J). Comparative studies on the strains both in qualitative and quantitative assay showed similar results, as the strains could easily be divided into two groups. These findings indicate that there is a correlation between qualitative and quantitative assay. However, in qualitative assay using NBRI-BPB it was possible to quickly distinguish the two groups of bacteria, without any need for time consuming biochemical methods usually involved in the quantitative assay of phosphate solubilisers. The results suggest that NBRI-BPB should serve as an excellent synergistic composition for the initial screening of large number of phosphate solubilisers.

EXAMPLE 2

Figure 3:
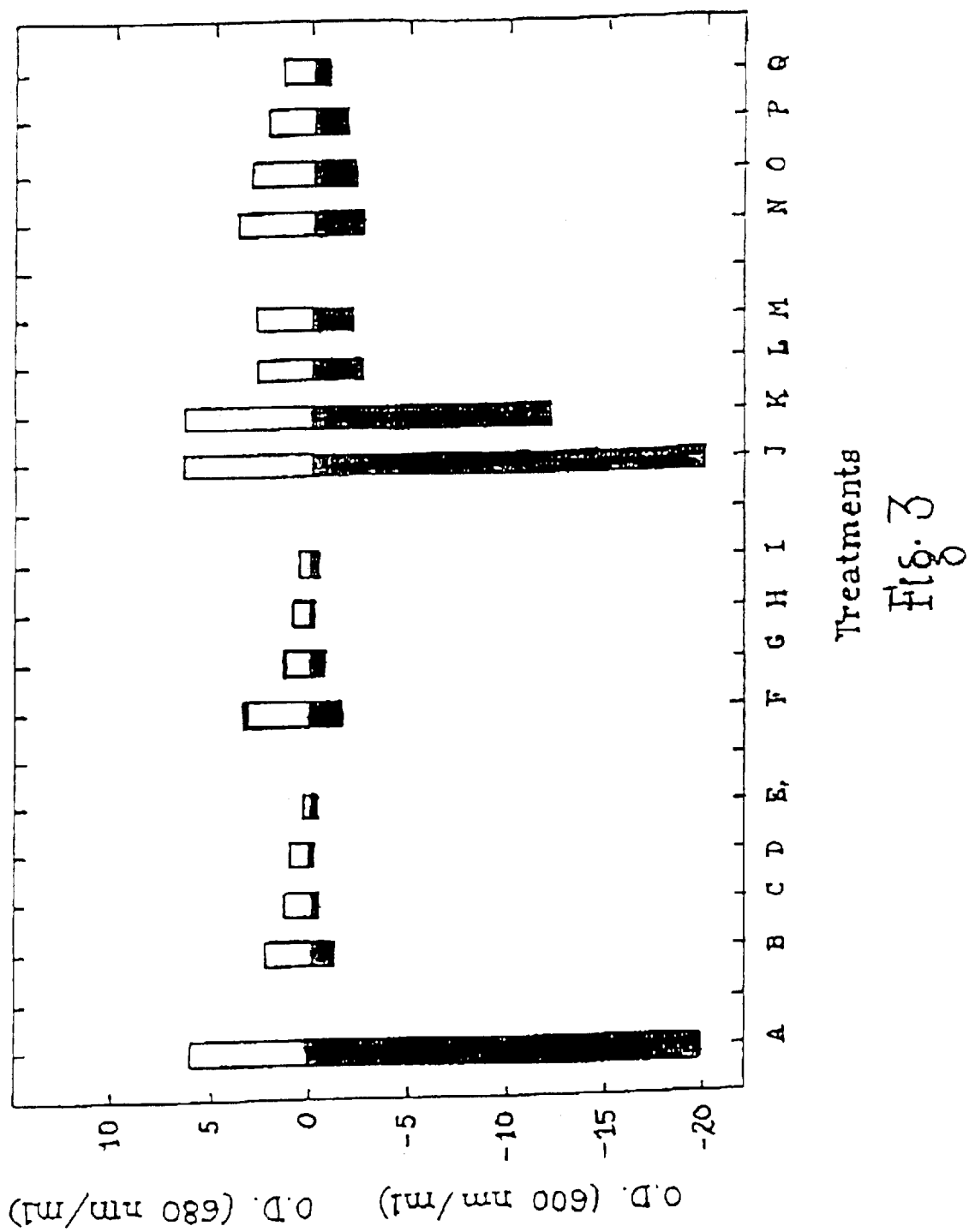
FIG. 3 shows Qualitative (■) and quantitative (□) analysis of effects of various carbon, nitrogen and salts.

An investigation was carried out to assess the probability of an early detection of the effect of various physiological parameters on qualitative and quantitative analysis, using NBRI-BPB. The results are shown in FIG. 3 of the drawing accompanying this specification. Qualitative (■) and quantitative (□) analysis of the effect of various carbon, nitrogen, and salts. To check the effect of carbon sources, glucose (A) in the NBRIP-BPB was replaced by the carbon source, arabinose (B), glycerol (C), xylose (D), fructose (E), as indicated. To check the effect of nitrogen sources, $(NH_4)_2SO_4$ (A) in the NBRIP-BPB was replaced by the nitrogen source, $(NH_4)2Cr_2O_7$ (F), $C_4H_{12}N_2O_6$ (G), $NH_4HCO_3$ (H), $C_{24}H_{20}Bi_4O_{28}.6NH_3.10H_2O$ (I), as indicated. To check the effect of salts, $MnCl_2.4H_2O$; 2.5 gm/Lt (J), $NaNO_3$; 2.5 gm/Lt (K), $CaCl_2.2H_2O$; 0.25 gm/Lt (L), $MnSO_4.H_2O$; 0.25 gm/Lt (M) was added in the NBRIP-BPB, as indicated. Tn5 mutants, ASLU13.T035 (N), ASLU13.T168 (O), ASLU13.T268 (P), and ASLU13.T483 (Q) were grown in NBRI-BPB medium, at 30° C., pH 7 for 3 days.

Phosphate solubilisation activity of ASLU13 was monitored in the presence of various carbon, nitrogen, and salts. ASLU13 as compared with control NBRI-BPB (FIG. 3A), demonstrated diverse level of phosphate solubilisation activity in the presence of various carbon [arabinose (FIG. 3B), glycerol (FIG. 3C), xylose (FIG. 3D), fructose (FIG. 3E)]; nitrogen [$(NH_4)2Cr_2O_7$ (FIG. 3F), $C_4H_{12}N_2O_6$ (FIG. 3G), $NH_4HCO_3$ (FIG. 3H), $C_{24}H_{20}Bi_4O_{28}.6NH_3.10H_2O$ (FIG. 3I)]; and salts [$MnCl_2.4H_2O$ (FIG. 3J), $NaNO_3$ (FIG. 3K), $CaCl_2.2H_2O$ (FIG. 3L), $MnSO_4.H_2O$ (FIG. 3M)]. The pattern of phosphate solubilisation by ASLU13 in qualitative assay using NBRI-BPB, correlated well with quantitative assay. This observation further augments well for the use of NBRI-BPB for qualitative analysis to detect the effect of various physiological factors on phosphate solubilisers, based upon visual observation. Pure culture evaluation using NBRI-BPB may be a useful tool in search of phosphate solubilizing strains better suited for soil environments where physiological factors may constitute a limitation for phosphate solubilisation.

EXAMPLE 3

An experiment was conducted to screen five hundred phosphate solubilisation defective Tn5 mutants of ASLU13. The results are shown in FIG. 3 of the drawing accompanying this specification. Qualitative (■) and quantitative (□) analysis of the phosphate solubilisation defective transposon5 (Tn5) mutants, ASLU 13 (A) and Tn5 mutants, ASLU13.T035 (N), ASLU13.T168 (O), ASLU13.T268 (P), and ASLU13.T483 (Q) were grown in NBRI-BPB medium, at 30° C. pH 7 for 3 days. Based upon visual observation, due to their incapability to decolorize BPB efficiently, as compared with ASLU13 (FIG. 3A), four mutants ASLU13.T035 (FIG. 3N), ASLU13.T168 (FIG. 3O), ASLU13.T268 (FIG. 3P), and ASLU13.T483 (FIG. 3Q) were easily distinguishable by 3 day. Quantitative analysis further confirmed the diverse levels of phosphate solubilisation ability of the mutants (FIG. 3). These findings further demonstrate that there is a correlation between the pattern of phosphate solubilisation by the mutants in qualitative assay and quantitative assay. The data thus show that using our simple protocol, it is indeed possible to screen large number of phosphate solubilizing defective mutants.

EXAMPLE 4

Phosphate solubilizing bacteria have been used in the commercial preparation of phosphate-dissolving cultures to improve the growth of plants [Tilak K V B R (1993) Bacterial Fertilisers. New Delhi, India: Indian Council of Agricultural Research; Subba Rao N S (1993) Biofertilizers in agriculture and forestry. Oxford & IBH Publishing Company Pvt. Ltd., New Delhi: Oxford & IBH Publishing Company Pvt. Ltd.]. Based on the observations obtained as above, a study was conducted to evaluate the possibility of using NBRI-BPB for quickly assessing the quality of commercial bioinoculant preparations, based on phosphate solubilsers. The results are shown in FIG. 3 of the drawing accompanying this specification. Qualitative (■) and quantitative (□) analysis of the ASLU13 (A, B, C) and various commercial bioinoculants, based on phosphate solubilsers, CPB1 (D, E, F), CPB2 (G, H. I), CPB3 (J. K, L), CPB4 (M, N, O), and CPB5 (P, Q, R), grown in NBRI-BPB medium, at 30° C., pH 7 for upto 1 day (A, D, G, J, M, P), 2 day (B, E, H, K, N, Q), and 3 day (C,F,I,L,O,R).

Figure 4:
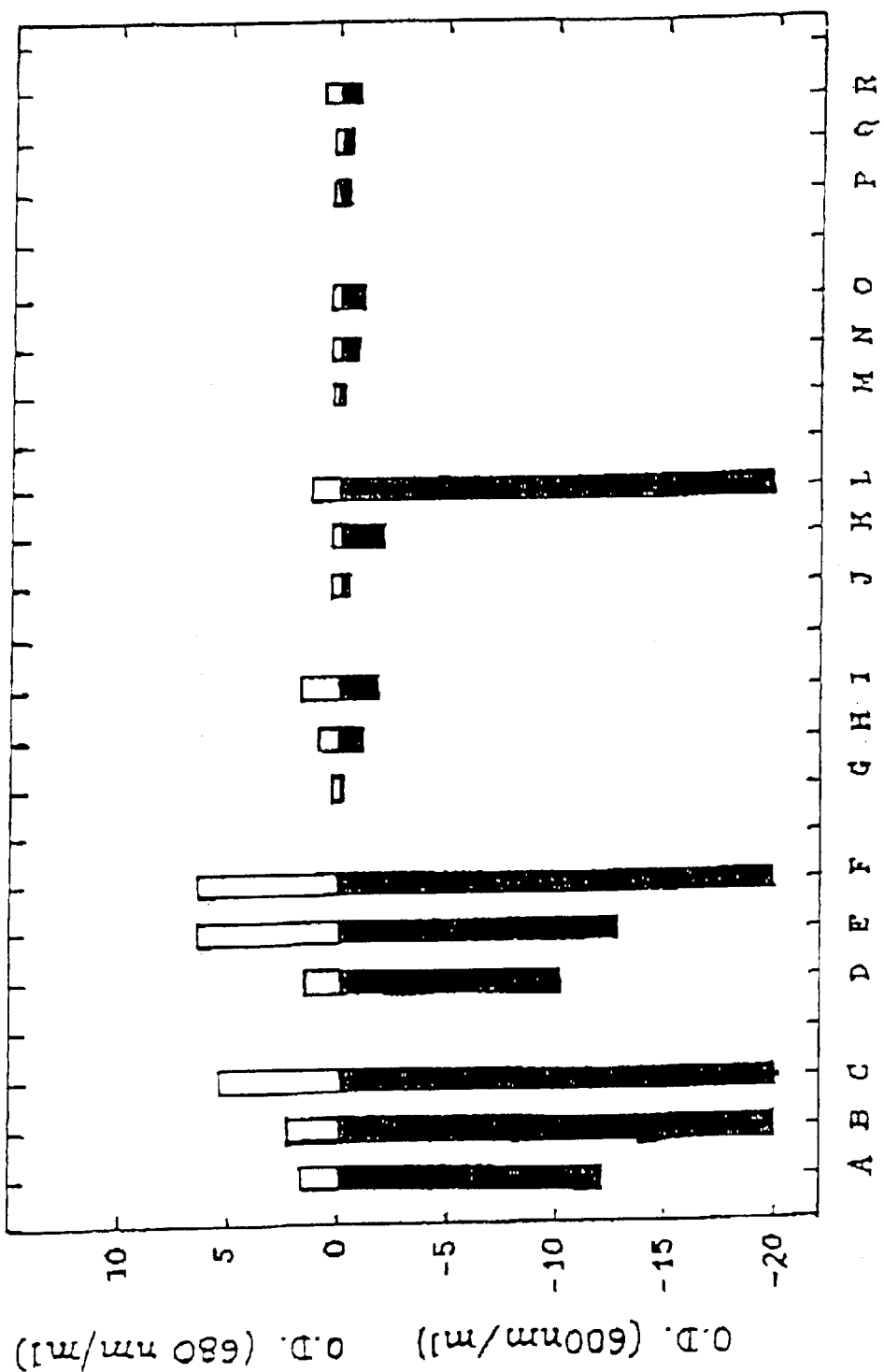
FIG. 4 shows Qualitative (■) and quantitative (□) analysis of the ASLU 13 (A,B,C) and various commercial bioinnoculants.

In a comparative study, using our ASLU13 based bioinoculant preparation (4A, 4B, 4C), along with five commercial products CPB1 (4D, 4E, 4F), CPB2 (4G, 4H, 4I), CPB3 (4J, 4K, 4L). CPB4 (4M, 4N, 4O), and CPB5 (4P, 4Q, 4R), grown in NBRI-BPB medium, at 30° C., pH 7 for upto 1 day (4A, 4D, 4G, 4J, 4M, 4P), 2 day (4 B, 4E, 4H, 4K, 4N, 4Q), and 3 day (4C, 4F, 4,I 4L, 4O, 4R), was subjected to testing by the new synergistic composition (FIG. 4). Decolorisation of BPB using our ASLU13 based bioinoculant preparation was achieved by 2 day (FIG. 4B). Among the five products tested, based upon visual observation the highest limit of decolorisation of BPB in products CPB1 (FIG. 4F) and CPB3 (FIG. 4L) was achieved by 3 day, while decolorisation of BPB in CPB2 (FIG. 4B), CPB4 (FIG. 4O), and CPB5 (FIG. 4R) was under −0.180 by 3 day. Thus the commercial bioinoculant product CPB1 was easily distinguishable from other products in its ability to solubilise phosphate. Furthermore, the present work indicates that the synergistic composition can also be used for expeditious screening of the commercial bioinoculant preparations, based on phosphate solubilsers.

Our results indicate that using our synergistic composition containing BPB, it is possible to quickly screen on qualitative basis, the phosphate solubilizing bacteria. Qualitative analysis of the phosphate solubilised by various groups, correlated well with grouping based upon quantitative analysis of bacteria isolated from soil, effect of various carbon, nitrogen, salts, and phosphate solubilisation defective transposon mutants. However, unlike quantitative analysis methods which involve time consuming biochemical procedures, the time for screening phosphate solubilizing bacteria is significantly reduced by using our simple protocol. Therefore, it is hereby suggested that this synergistic composition based upon qualitative analysis should be used for the quick screening of phosphate solubilizing bacteria. Our results indicate that the synergistic composition can also be used for expeditiously screening the commercial bioinoculant preparations, based on phosphate solubilsers.

The main advantages of the synergistic composition of the present invention are:

1. It can be used for quick screening of phosphate solubilizing microorganisms, because our protocol is based upon visual observation.

2. The novel synergistic composition of the present invention NBRIP-BPB broth assay, can be used for the qualitative analysis of bacteria isolated from soil, effect of various carbon, nitrogen, salts, and phosphate solubilisation defective transposon mutants.
carbon, nitrogen, salts, and phosphate solubilisation defective mutants.

3. The synergistic composition can also be used as a quality control test for expeditious screening of the commercial bioinoculant preparations, based on phosphate solubilsers.

What is claimed is:

1. A growth medium composition for screening a phosphate solubilizing microorganism, comprising:

| | |
|---|---|
| Glucose | 5 to 30 grams/liter; |
| $Ca_3(PO_4)_2$ | 1 to 20 grams/liter; |
| $MgCl_2.6H_2O$ | 0.5 to 20 grams/liter; |
| $MgSO_4.7H_2O$ | 0.05 to 5 grams/liter; |
| KCl | 0.025 to 5 grams/liter; |
| $(NH_4)_2SO_4$ | 0.01 to 2 grams/liter; and |
| bromophenol blue (BPB) | 0.01 to 0.1 grams/liter. |

2. The composition of claim 1, comprising:

| | |
|---|---|
| Glucose | 10 grams/liter; |
| $Ca_3(PO_4)_2$ | 5 grams/liter; |
| $MgCl_2.6H_2O$ | 5 grams/liter; |
| $MgSO_4.7H_2O$ | .25 grams/liter; |
| KCl | 0.2 grams/liter; |
| $(NH_4)_2SO_4$ | .01 grams/liter; and |
| BPB | 0.025 grams/liter. |

3. The composition of claim 1 wherein at least one ingredient used in the composition is commercial grade.

4. A method of using the composition of claim 1 comprising:
qualitatively analyzing an organism or mutant utilizing said composition for the qualitative analysis of at least one microorganism, or for the qualitative analysis of at least one carbon, nitrogen, salt or phosphate solubilization—defective transposon mutant.

5. A kit for the screening of a phosphate solubilizing microorganism, said kit comprising the growth medium composition of claim 1.

6. A method for screening at least one phosphate solubilizing microorganism comprising:
screening an organism utilizing a growth medium composition comprising bromophenol blue (BPB) in an amount of 0.01 to 0.1 grams/liter.

7. The method of claim 6 wherein the growth medium composition comprises:

| | |
|---|---|
| Glucose | 5 to 30 grams/liter; |
| $Ca_3(PO_4)_2$ | 1 to 20 grams/liter; |
| $MgCl_2.6H_2O$ | 0.5 to 20 grams/liter; |
| $MgSO_4.7H_2O$ | 0.05 to 5 grams/liter; |
| KCl | 0.025 to 5 grams/liter; |
| $(NH_4)_2SO_4$ | 0.01 to 2 grams/liter; and |
| BPB | 0.01 to 0.1 grams/liter. |

8. The method of claim 6 wherein the growth medium composition comprises:

| | |
|---|---|
| Glucose | 10 grams/liter; |
| $Ca_3(PO_4)_2$ | 5 grams/liter; |
| $MgCl_2.6H_2O$ | 5 grams/liter; |
| $MgSO_4.7H_2O$ | 0.25 grams/liter; |
| KCl | 0.2 grams/liter; |
| $(NH_4)_2SO_4$ | 0.1 grams/liter; and |
| BPB | 0.025 grams/liter. |

9. The method of claim 6 comprising:
growing the microorganism in the growth medium to obtain a culture.

10. The method of claim 6 comprising:
harvesting the culture to obtain a supernatant.

11. The method of claim 6 comprising:
measuring an optical density of the supernatant.

12. The method of claim 11, wherein the optical density is measured by quantifying light absorbance at 600 nm.

13. The method of claim 6, wherein the growth medium composition comprises:

| | |
|---|---|
| Glucose | 5 to 30 gm/liter; |
| $Ca_3(PO_4)_2$ | 1 to 20 gm/liter; |
| $MgCl_2.6H_2O$ | 0.5 to 20 gm/liter; |
| $MgSO_4.7H_2O$ | 0.05 to 5 gm/liter; |
| KCl | 0.025 to 5 gm/liter; |
| $(NH_4)_2SO_4$ | 0.01 to 2 gm/liter; and |
| BPB | 0.01 to 0.1 gm/liter. |

14. A kit for the screening of phosphate solubilizing microorganisms, said kit comprising a growth medium composition comprising:

| | |
|---|---|
| Glucose | 10 grams/liter; |
| $Ca_3(PO_4)_2$ | 5 grams/liter; |
| $MgCl_2.6H_2O$ | 5 grams/liter; |
| $MgSO_4.7H_2O$ | 0.25 grams/liter; |
| KCl | 0.2 grams/liter; |
| $(NH_4)_2SO_4$ | 0.1 grams/liter; and |
| bromophenol blue (BPB) | 0.025 grams/liter. |

15. A method for screening at least one phosphate solubilizing microorganism comprising:

a) growing the microorganism in a growth medium composition comprising bromophenol blue (BPB) in an amount of 0.01 to 0.1 grams/liter to obtain a culture;

b) harvesting the culture to obtain a supernatant;

c) measuring an optical density of the supernatant.

* * * * *